US00RE47368E

(19) United States
(12) Reissued Patent
Greenberg

(10) Patent Number: US RE47,368 E
(45) Date of Reissued Patent: Apr. 30, 2019

(54) MODULAR TEMPLATE FOR DRILLING HOLES AND METHOD OF MAKING SAME

(71) Applicant: Greenberg Surgical Technologies, LLC, New York, NY (US)

(72) Inventor: Alex M. Greenberg, New York, NY (US)

(73) Assignee: Greenberg Surgical Technologies, LLC, New York, NY (US)

(21) Appl. No.: 15/615,417

(22) Filed: Jun. 6, 2017

Related U.S. Patent Documents

Reissue of:
(64) Patent No.: 9,050,665
Issued: Jun. 9, 2015
Appl. No.: 11/438,217
Filed: May 22, 2006

U.S. Applications:
(63) Continuation-in-part of application No. 11/157,882, filed on Jun. 21, 2005, now Pat. No. 7,513,722, and (Continued)

(51) Int. Cl.
*A61B 17/17* (2006.01)
*A61C 1/08* (2006.01)
*B23B 47/28* (2006.01)

(52) U.S. Cl.
CPC ..... *B23B 47/28* (2013.01); *A61B 17/176* (2013.01); *A61C 1/084* (2013.01); *A61B 17/1703* (2013.01);

(Continued)

(58) Field of Classification Search
CPC ..... A61C 1/084; A61C 1/082; B23B 47/28; A61B 17/176; A61B 17/1703; Y19T 408/8925

(Continued)

(56) References Cited

U.S. PATENT DOCUMENTS 1,372,378 A * 3/1921 Walker ..... 408/115 R
1,417,236 A * 5/1922 Evans ..... 433/75

(Continued)

FOREIGN PATENT DOCUMENTS

WO WO 99/32045 7/1999
WO WO 03/071972 9/2003

(Continued)

OTHER PUBLICATIONS

English translation of Japanese Office Action for JP Application No. 2008-512594.

(Continued)

*Primary Examiner* — Cary E Wehner
(74) *Attorney, Agent, or Firm* — Cozen O'Connor

(57) ABSTRACT

A template for use with an instrument to drill a hole in a surface at a desired location. The template includes a body which has a negative impression of the surface, and a guideway having a first end positioned to open onto the desired location when the body is placed in conforming contact with the surface and a second end positioned on an exterior surface of the body. The second end of the guideway is connected to the first end by a passage. The guideway is preferably positioned in a portion of the template which is removable from the remainder thereof. The template also includes a stop for limiting the depth of penetration of the drill bit into the hole, a first fastener for attaching the stop to the body and a second fastener for fastening the removable portion of the template to the remainder of the template.

22 Claims, 4 Drawing Sheets

Related U.S. Application Data a continuation-in-part of application No. 10/748,338, filed on Dec. 30, 2003, now Pat. No. 7,210,881.

(60) Provisional application No. 60/683,050, filed on May 20, 2005.

(52) U.S. Cl.
CPC ..... *A61C 1/082* (2013.01); *Y10T 408/8925* (2015.01)

(58) Field of Classification Search
USPC ..... 606/89 R, 57, 96; 433/72, 75, 173, 176; 408/72 B, 115 R, 115 B, 97, 110, 241 B
See application file for complete search history.

(56) References Cited

U.S. PATENT DOCUMENTS

| | | | | | |
|---|---|---|---|---|---|
| 1,545,424 | A | | 7/1925 | Heimrich | |
| 1,946,421 | A | * | 2/1934 | Brown, Jr. | 408/62 |
| 2,710,454 | A | * | 6/1955 | Kershaw | 33/669 |
| 2,929,277 | A | * | 3/1960 | Hagen | 408/97 |
| 2,949,798 | A | | 8/1960 | Berta, Jr. | |
| 3,082,651 | A | | 3/1963 | Patrick, Jr. | |
| 3,414,975 | A | * | 12/1968 | Small | 433/75 |
| 3,919,722 | A | | 11/1975 | Lenczycki | |
| 3,919,772 | A | * | 11/1975 | Lenczycki | 433/173 |
| 4,325,373 | A | * | 4/1982 | Slivenko et al. | 606/96 |
| 4,346,508 | A | * | 8/1982 | Baumann et al. | 29/402.18 |
| 4,421,442 | A | * | 12/1983 | Lindblad | 408/115 R |
| 4,474,514 | A | * | 10/1984 | Jensen | 408/115 R |
| 4,538,354 | A | * | 9/1985 | Smolik | 408/72 B |
| 4,544,307 | A | * | 10/1985 | Miller | 408/72 B |
| 5,116,345 | A | * | 5/1992 | Jewell et al. | 606/130 |
| 5,318,391 | A | * | 6/1994 | Breiner | 408/103 |
| 5,366,326 | A | * | 11/1994 | Converse | 408/72 B |
| 5,624,447 | A | * | 4/1997 | Myers | 606/96 |
| 5,655,330 | A | | 8/1997 | Parsons, III | |
| 5,730,560 | A | * | 3/1998 | Marcelloni | 408/72 B |
| 5,733,077 | A | * | 3/1998 | MacIntosh, Jr. | 408/103 |
| 5,797,741 | A | * | 8/1998 | Bonpard et al. | 433/75 |
| 5,800,168 | A | | 9/1998 | Cascione et al. | |
| 5,989,025 | A | * | 11/1999 | Conley | 433/76 |
| 6,398,783 | B1 | | 6/2002 | Michelson | |
| 6,902,401 | B2 | * | 6/2005 | Jorneus et al. | 433/173 |
| 2002/0168237 | A1 | * | 11/2002 | Cline et al. | 408/1 R |
| 2003/0186187 | A1 | * | 10/2003 | Germanier | 433/75 |
| 2004/0153087 | A1 | * | 8/2004 | Sanford et al. | 606/88 |
| 2005/0170311 | A1 | * | 8/2005 | Tardieu et al. | 433/76 |

FOREIGN PATENT DOCUMENTS

| | | | | |
|---|---|---|---|---|
| WO | WO/2004/075771 | | 9/2004 | |
| WO | WO-2004/075771 | A1 * | 9/2004 | |
| WO | WO 2004075771 | A1 * | 9/2004 | A61C 13/00 |
| WO | WO 2004/098435 | | 11/2004 | |

OTHER PUBLICATIONS

Daniel Van Steenberghe, MD. et al., A Custom Template and Definitive Prosthesis Allowing Immediate Implant Loading in the Maxilla: A Clinical Report, The International Journal of Oral & Maxillofacial Implants pp. 663-670, vol. 17, No. 5, 2002.

R Jacobs et al., Predictability of a three-dimensional planning system for oral implant surgery, Dentomaxillofacial Radiology (1999) 28, 105-111 1999 Stockton Press.

EP Office Action dated Dec. 4, 2012 issued in corresponding application No. 06 770 839.6.

PCT—Written Opinion of the International Searching Authority dated Feb. 9, 2007 (Form PCT/ISA/237).

PCT—Notification of Transmittal of the International Search Report and the Written Opinion to the International Searching Authority, or the Declaration dated Feb. 9, 2007 (Form PCT/ISA/220).

* cited by examiner

MODULAR TEMPLATE FOR DRILLING HOLES AND METHOD OF MAKING SAME

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS-REFERENCE TO RELATED APPLICATIONS

This application *is a Reissue of U.S. Pat. No. 9,050,665, which* claims priority from U.S. Provisional Patent Application Ser. No. 60/683,050 filed May 20, 2005, and is a continuation-in-part of non-provisional patent application Ser. No. 11/157,882, filed Jun. 21, 2005 now U.S. Pat. No. 7,513,722, and Ser. No. 10/748,338, filed Dec. 30, 2003 now U.S. Pat. No. 7,210,881.

1. FIELD OF THE INVENTION

This application is directed to the field of manufacturing processes and, more particularly, to the field of modular manufacturing processes for use in preparing a template for use in drilling.

BACKGROUND OF THE INVENTION

Drills are used in many fields, from carpentry to dentistry, and must be used with care, lest the drill make a hole which cannot be repaired. This is especially true in medical fields, where the surface to which the drill is applied is that of a living creature, and an improperly drilled hole may have catastrophic and irreparable consequences.

There is thus always a concern in using drills, and especially in using medical drills, that any plan for drilling is based on the best and most accurate information available, and that any drilling be done only after the procedure is planned down to the smallest detail. For example, X-rays may be taken of a patient's leg to determine the location of a fracture, so that setting pins may be inserted correctly and with minimum invasiveness.

Another application, and one with which the invention is primarily focused, is in the field of dental drilling and implants. In this field, it is customary for a dental surgeon to take X-rays of a patient's jaw prior to surgery and plot out carefully where an implant will be located. Known systems involve taking radiographic pictures of a patient's jaw, and determining, based on the radiograph, precisely where a hole will be drilled, how deep the hole will be, at what angle, and with what diameter. It is customary to make an impression of a patient's jaw, and then use that impression to make a template of the planned hole, with a guide for where the surgeon should drill.

These known systems, while mostly effective, also suffer from some drawbacks.

For one, when depending upon radiographs, such as X-rays, some imprecision may result from scatter caused by pre-existing dental work, such as amalgams or crowns, in the patient's mouth. Even small amounts of scatter may affect the accuracy of the resulting picture of the patient's jaw, and therefore lessen the accuracy of the resulting template.

A prior United States Patent Application, Ser. No. 2005/084144 entitled Oral Implant Template, the disclosure of which is hereby incorporated by reference, sought to address some of these deficiencies. This application describes the use of a process by which a Computed Tomography ("CT") scan is made of a patient wearing a radiographic template on the jaw. The radiographic template carries a plurality of radiographic markers. After the scan of the jaw is obtained, a second scan is made of the radiographic template alone. The two data sets are then merged by using the radiographic markers as points of alignment. The result is that the radiographic template has the memory of the negative impression of the teeth which is registered in the CT scan data and allows for a replication of the tooth form with an accuracy that would otherwise be unobtainable. Based on the image and information thus obtained, the practitioner decides on the appropriate trajectory and location of the dental implant. With this data, the radiographic template is converted into a virtual surgical template with appropriate trajectories positioned at the correct locations where drilling guideways for the dental implants will be placed. Holes are indicated in the virtual surgical template at the desired locations and at the desired trajectories into which metal sleeves are inserted to guide the surgeon in the procedure. The virtual surgical template is then used to manufacture a surgical template which is inserted in the patient's mouth for precise placement of dental implants in the jaw bone via a drilling and insertion procedure.

This resulting surgical template forward from the virtual template, while offering an improvement over the prior art, still suffers from some drawbacks. For example, it provides no means for limiting the depth of penetration of the drill into the target surface. Particularly in the field of dental implants, where the target surface is a human jawbone, controlling the depth of penetration of the drill is of vital importance.

The inventor herein has prior patents in the field of stops for dental drill bits, for example U.S. Pat. Nos. 5,888,034 and 5,746,743, the disclosures of which are hereby incorporated by reference. These patents disclose various forms of stops for drill bits for limiting the depth of penetration of drill bits into a surface, especially dental drill bits used to limit the depth of penetration of dental drills into the human jaw. These patents also describe the use of an adjustable sleeve and ferrules to limited the depth of penetration of a drill bit and accommodate different drill diameters and lengths. Furthermore, the insertion of ferrules of different diameters allows the use of a single surgical template with drill bits of varying diameters, rather than a series of surgical templates with different guide sleeve widths which saves considerable cost.

These patents, however do not disclose any means for producing a drilling template for use in preparing for drilling into a surface.

SUMMARY OF THE INVENTION

It is therefore an object of the invention to provide an improved template for use with surgical instruments which overcomes the drawbacks of the prior art.

It is another object of the invention to provide an improved modular manufacturing process for manufacturing drilling guides for use in conjunction with stops to control the location, trajectory and depth of penetration of a drill bit.

It is a further object of the invention to provide a manufactured template for inserting an instrument into a surface which includes means for accepting a pre-formed stop for limiting the depth of penetration of the instrument into the surface.

It is an additional object of the invention to provide a modular manufacturing method that will allow the placement of an immediate provisional/temporary fixed bridge on implants placed in the jaw utilizing the surgical template.

In accordance with these and other objects of the invention, there is provided a method for modular manufacturing of the portion of a surgical template which contains a guideway therein by creating a specially designed radiographic template that has a portion that is made of a modular material formed of acrylic, silicone, or other suitable radiotransparent materials that can be easily removed from the radiographic template and then separately scanned. Within the original radiographic template, at least six modular portion metallic markers are placed. The patient is sent for a CT scan with the original radiographic template and then the modular portion of the radiographic template is removed and scanned separately. The two data sets are merged using a computer program disclosed in the referenced published U.S. Patent Application No. 2005/0084144 using the radiographic markers as the points of alignment. The practitioner decides on the appropriate trajectory of the instrument (drill, probe, needle, etc.) and allows software to convert the data of the modular radiographic template into a modular surgical template with appropriate trajectories (guideways) prepared in the correct sites through which the instrument will be placed in the body cavity. The virtual surgical template is sent via e-mail or burned CD ROM to the manufacturer for a rapid manufacturing process that results in production of the modular surgical template that is then inserted into the original radiographic template modular site.

Briefly stated, the template so described includes a body which has a negative impression of the surface, and a guideway having a first end positioned to open onto a desired location on the surface when the body is placed in conforming contact with the surface and a second end positioned on an exterior surface of the body. The second end of the guideway is connected to the first end by a preferably substantially linear passage which is positioned to define the desired trajectory of the hole to be drilled. The guideway is preferably positioned in a portion of the template which is removable from the remainder thereof. The template may also include a stop for limiting the depth of penetration of the instrument into the surface, a first fastener for attaching the stop to the body and a second fastener for fastening the removable portion of the template to the remainder of the template.

This template can also be used in neurosurgery wherein a head frame is bolted to a patient's cranium for sterotactic surgery. In such an application, a CT scan is obtained before surgery and then, using adjustments on a head frame, mounted on the exterior of the patient's cranium, the practitioner determines the desired trajectory into the brain to allow the insertion of a suitable surgical instrument. To use this improved method of relating a radiographic template to the brain, a plastic helmet or reduced plastic sectional/regional template is attached to a head frame that is bolted to the cranium. A modular portion of the template is positioned within the region of the cranium where the surgical procedure is anticipated to be performed. The modular portion is preferably made of a material such as acrylic, silicone, or other suitable radiotransparent materials that can be easily removed from the radiographic template, and includes at least six radiographic markers. The patient has a CT scan while wearing the original radiographic template containing the modular portion. After this scan, the modular portion of the original radiographic template is removed and scanned separately. The two data sets are compared, and the practitioner decides on the appropriate trajectory of the surgical instrument, thereby creating a virtual surgical template having appropriate trajectories located in the correct sites through which the surgical instrument will be placed in the body cavity.

The virtual surgical template is sent to a manufacturer for the production of the physical modular surgical template that will actually be inserted into the original radiographic template modular site. The modular part that is insertable and removable from the plastic helmet or sectional template has the appropriate trajectories (guideways) prepared in the correct sites through which the suitable surgical instrument will be placed in the body cavity. This modular portion is then reinserted into the original radiographic template for the surgical procedure to then be performed.

In any of the processes, the surgical template may also include a stop affixed to the template to limit the depth to which any instrument may be inserted into the body cavity.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

BRIEF DESCRIPTION OF THE DRAWINGS

In the drawings, in which like numerals depict like elements.

DETAILED DESCRIPTION OF THE PRESENTLY PREFERRED EMBODIMENTS

The inventive template is intended for use with an instrument, such as a drill bit, probe or needle, to provide guidance to the instrument for entering a hole in a surface at a desired location, at a desired trajectory, to a desired depth. In the preferred embodiment, the ultimate purpose of the template is to assist in a surgical drilling procedure, and the surface is part of a body, likely (but not necessarily) human. In the most preferred embodiment, the surgical procedure is part of the procedure for placing a dental implant in a human jaw bone, but one of ordinary skill in the art will appreciate that the procedure has a wider applicability, and is not limited to surgical procedures in general, or dental procedures in the specific.

The basic method of manufacturing a template in accordance with the invention is described in detail in the United States Published Patent Application Publ. No. 2005/0084144 and will not be repeated at length, here.

Figure 1:
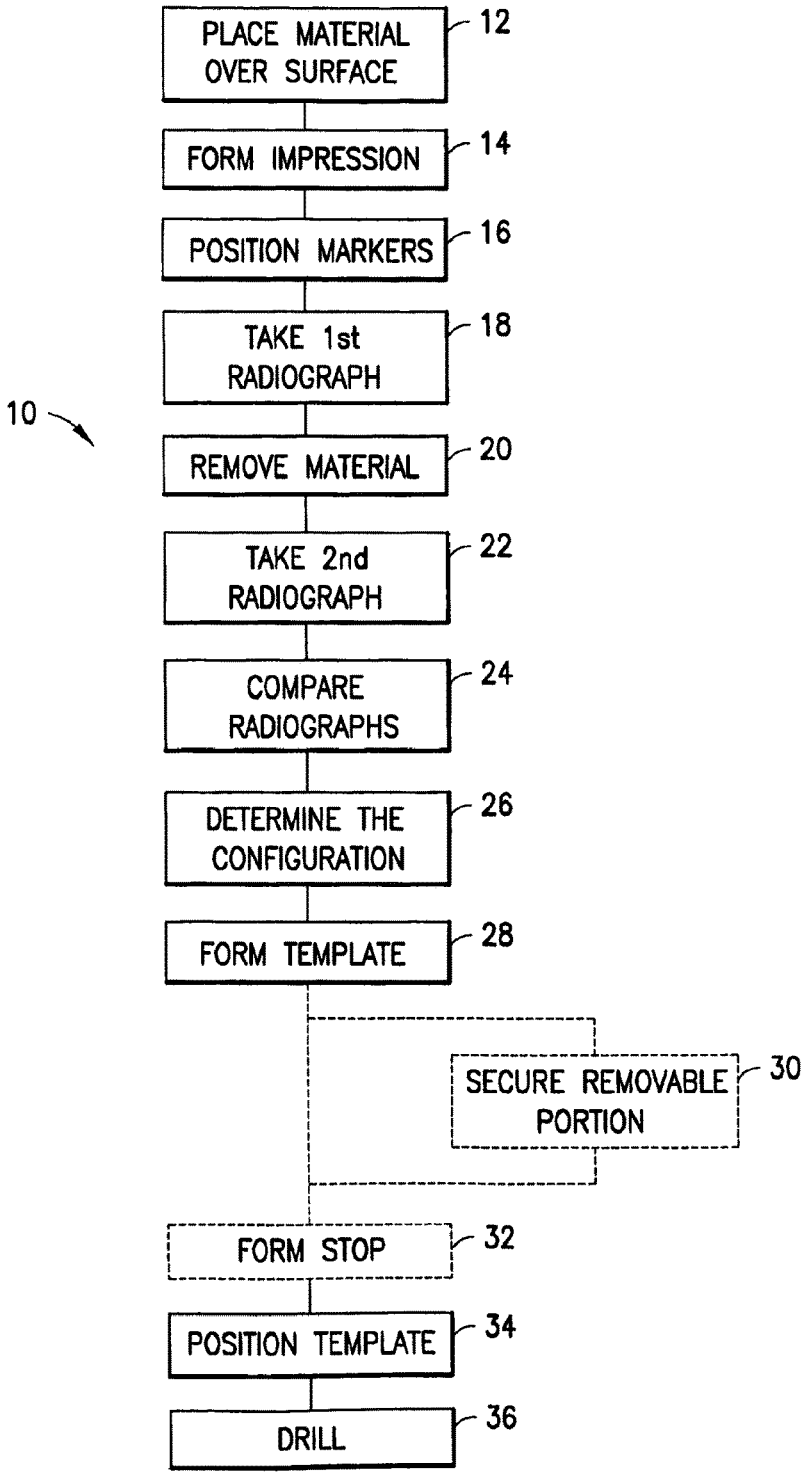
FIG. 1 is a block diagram showing the steps of the inventive method.

Briefly, as shown in FIG. 1, the method (designated generally at 10) of manufacturing a template in accordance with the invention includes the following steps:

Placing a substantially radio-transparent malleable material and a plurality of radio-opaque markers in contact with the surface into which the instrument is to be inserted (12). Suitable materials for use as the template include acrylic and silicone.

Forming a negative impression of the surface by conforming the malleable material to a portion of the surface, in the vicinity of the location at which the hole is or will be located (14).

Positioning the markers at defined positions in the maleable material in contact with the surface (16).

Taking a first radiograph of the surface and the malleable material together (18).

Removing the malleable material from the surface (20).

Taking a second radiograph of the negative impression apart from the surface (22).

Comparing the first and second radiographs to determine the shape of the surface (24).

Determining the configuration of the guideway to be placed in the template, depending upon the desired location of the hole in the surface, the desired trajectory for the instrument to enter the hole, and the desired maximum depth of penetration of the instrument into the hole (26).

Forming a template for use with the instrument (28). The template conforms to the negative impression and includes a guideway for the instrument through the template along the desired trajectory, and positioned so that the instrument passes through the guideway to reach the surface at the desired location to enter or form the hole. In one embodiment of the invention, the template includes a removable portion, and the guideway is positioned within the removable portion. In this embodiment, there is an additional step (30) of securing the removable portion to the remainder of the template.

In another embodiment of the invention, there is a still further step (32) of positioning a stop in the template to limit the depth of penetration of the instrument into the hole to the desired depth.

In any embodiment, at this point the template may be positioned (34) on the surface, with the negative impression holding the template in place, and the guideway establishing the proper location and trajectory for the instrument.

The user may then begin to use the instrument, such as to begin drilling (36) through the surface. If a stop is used, the user may insert the instrument until the stop prevents further forward progress, thereby limiting the depth to which the instrument may enter the hole, and defining the maximum depth of penetration of the instrument into the surface. In the case of use of the template with a drill bit, this means that the positioning of the stop limits the maximum depth of a hole drilled into the surface.

In yet another embodiment, the template includes both a stop and a removable portion containing the guideway, and so both steps 30 and 32 may be performed in the same embodiment.

Figure 2:
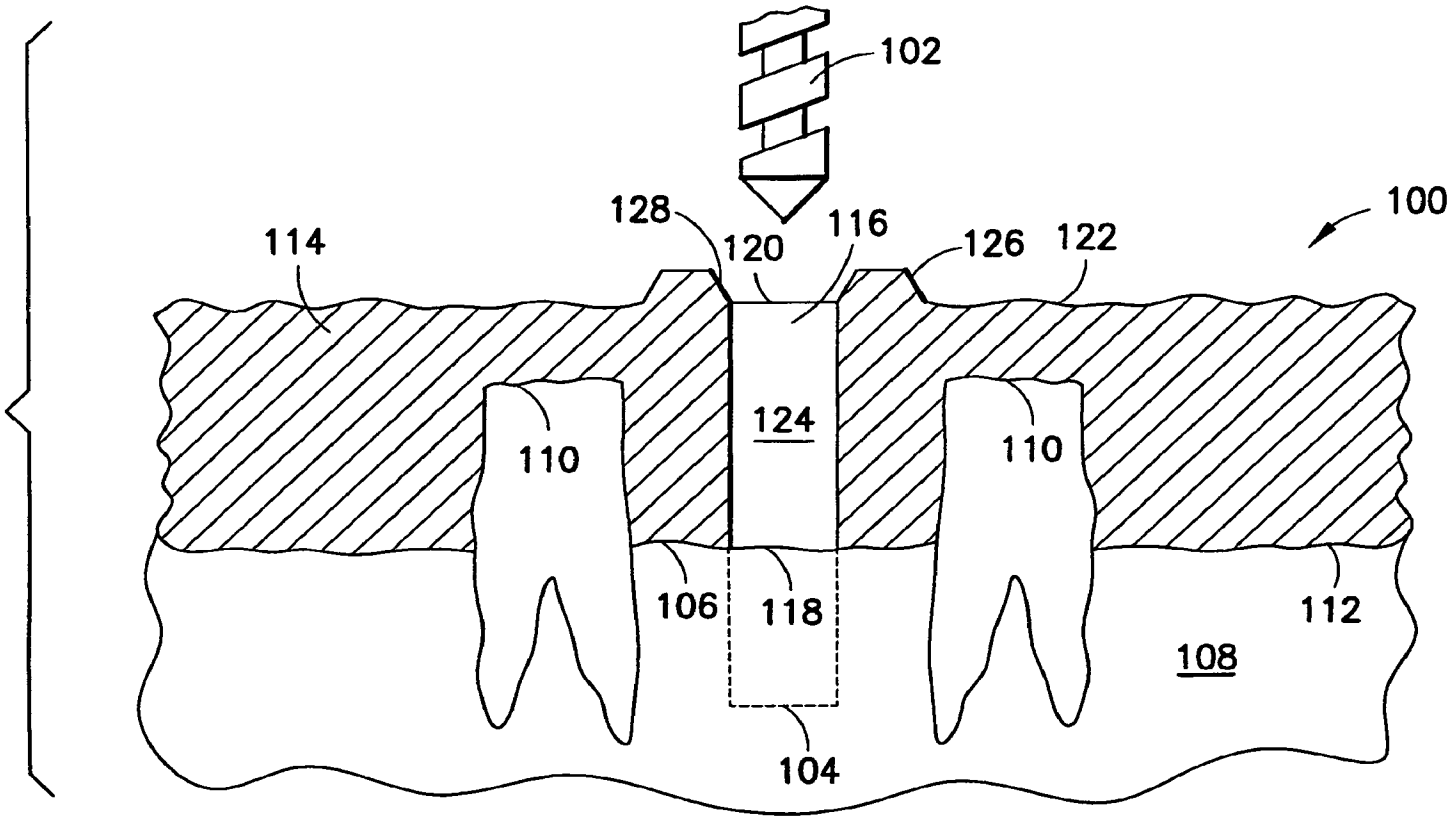
FIG. 2 is a cross-section of a template formed in accordance with the invention.

A template manufactured in accordance with the inventive method is shown in FIG. 2, generally at 100. Template 100 is intended for use with an instrument, such as drill bit 102 to drill a hole 104 (shown in dashed line) into a surface 106. In this illustration, surface 106 is a human jaw 108, which includes teeth 110 in the vicinity of the desired location for hole 104. In other dental embodiments, it may be desired to drill into the teeth directly, for example to treat a cavity, or to drill into some other kind of surface, such as a bone in another part of the body, for example the skull, or in an animal's bone in veterinary applications. It is even possible for the inventive template to be used in a completely different type of application, not involving surgery or drilling into a body, e.g., in carpentry applications, etc. These applications will be known and appreciated by those of ordinary skill in the art, and it is not the inventor's intention to limit the broad disclosure hereof by the particular illustrated embodiment.

According to the embodiment of the invention illustrated in FIG. 2, template 100 is made of any suitable malleable material, which is formed about surface 106 to form a negative impression 112 of surface 106 therein. Template 100 includes a body 114, having a guideway 116 formed therein. Guideway 116 has a first end 118 positioned to open onto the desired location for hole 104 when body 114 is placed in conforming contact with surface 106 and a second end 120 positioned on an exterior surface 122 of body 102. Second end 120 is connected to first end 118 by a passage 124. In a preferred embodiment, passage 124 is substantially linear. Template 100 also includes a stop 126 for limiting the depth of penetration of drill bit 102 into hole 104. Stop 128 may include a shoulder 128 configured to act as a countersink for centering drill bit 102 in guideway 116.

Figure 3:
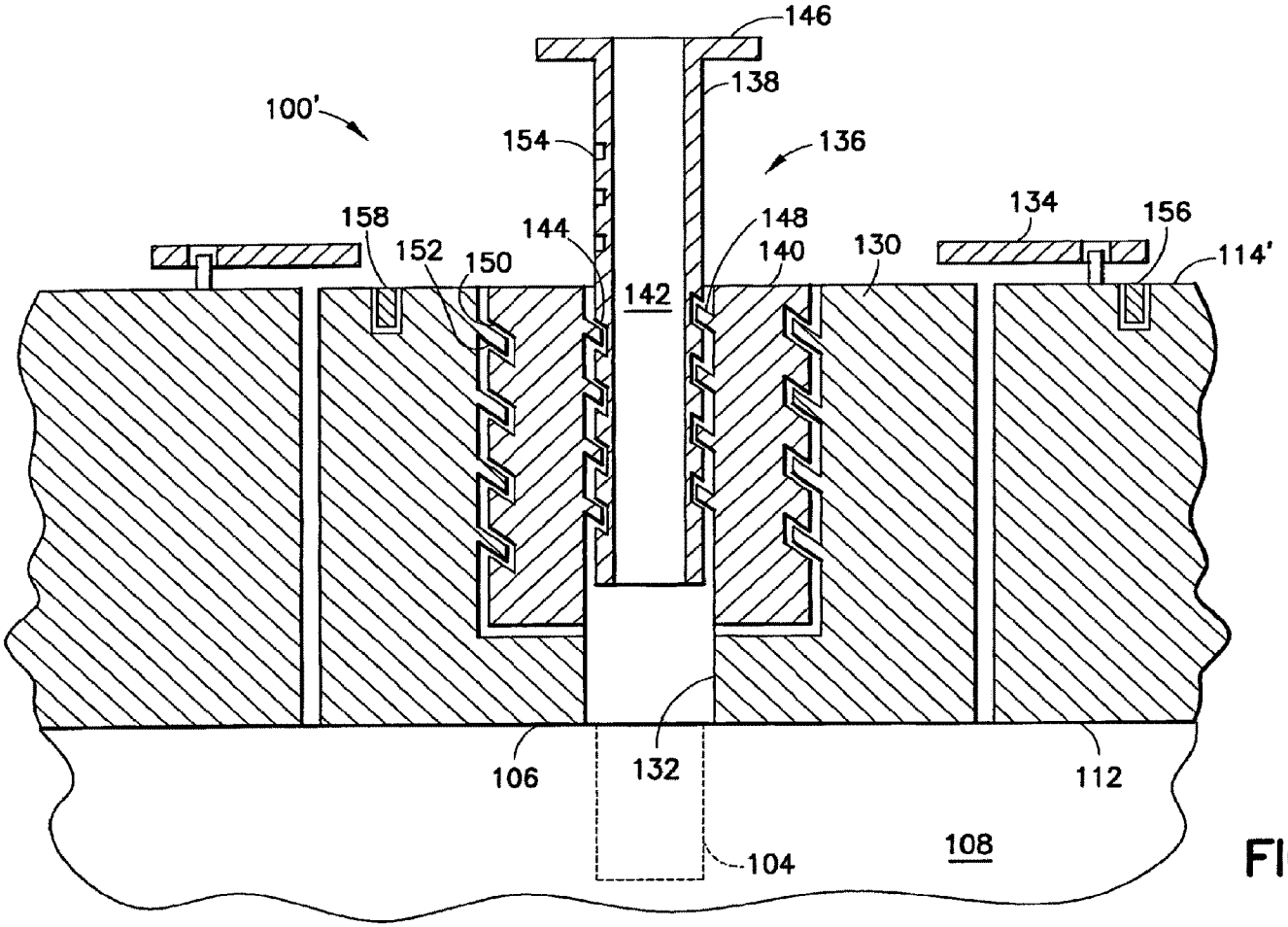
FIG. 3 is a cross-section of a detail of an alternate embodiment of the inventive template.

In an alternative embodiment, shown in FIG. 3, body 114' includes a removable portion 130 in which a guideway 132 is formed. Removable portion 130 may be fastened to body 114' by any suitable fastener, such as by at least one clip 134. In this embodiment, the drill bit (not shown in FIG. 2) will be guided by a guiding assembly 136 inserted in guideway 132. Guiding assembly 136 includes an inner piece 138, and an outer piece 140. Inner piece 138 has a substantially linear passage 142 centrally disposed therein for guiding the drill bit, a threaded outer surface 144 and a shoulder 146 which acts as a stop for the drill bit. Outer piece 140 includes a threaded inner surface 148 configured to engage the threads on threaded outer surface 144 of inner piece 138, and a threaded outer surface 150.

Removable portion 130 includes a threaded inner surface 152, having threads configured to engage the threads on outer surface 150 of outer piece 140. In this fashion, outer piece 140 may be fastened in removable portion 130 by screwing it thereinto. Inner piece 138 may then be screwed into outer piece 140 until shoulder 146 reaches the desired position to act as a stop for the drill bit. To assist in determining the depth of inner piece 138 within outer piece 140, indicia 154 may be provided on the outer surface of inner piece 138.

In one embodiment, the threads of outer surface 146 of outer piece 140 and the threads on inner surface 146 preferably have different pitches, so that one of inner piece 138 and outer piece 140 can act as a fine adjustment means for adjusting the depth of guiding assembly 136 in guideway 132, and the other of inner piece 138 and outer piece 140 can act as a coarse adjustment means therefor. In this fashion, it is possible to provide for better adjustment of the depth of guiding assembly 136 in guideway 132, as taught in my co-pending application Ser. No. 10/748,338, filed Dec. 30, 2003, the disclosure of which is hereby incorporated by reference.

Alternatively, it is possible that the two threads could have equal pitches, simply to provide for adjustment of the positioning of shoulder 146 relative to surface 106, and therefore adjust the depth to which the drill bit will drill hole 104.

It is further preferred that inner and outer pieces 138 and 140 be made of a durable material, such as a metal, so that any contact of the drill bit therewith will not result in a widening of passage 142, and the possible mis-alignment of hole 104 from its desired location.

In another embodiment of the invention, body 114' may be formed to include radiographic markers 158. These markers may be removable or permanently affixed, to body 114', as desired. Placing radiographic markers 156, 158 in body 114' and removable portion 130, respectively, offers the benefit of allowing surgical template 100' to act also as a radiographic template, in case further radiographs are useful in preparing subsequent replaceable portions 130.

The inventive method is useful in many applications other than those explicitly described.

Figure 4:
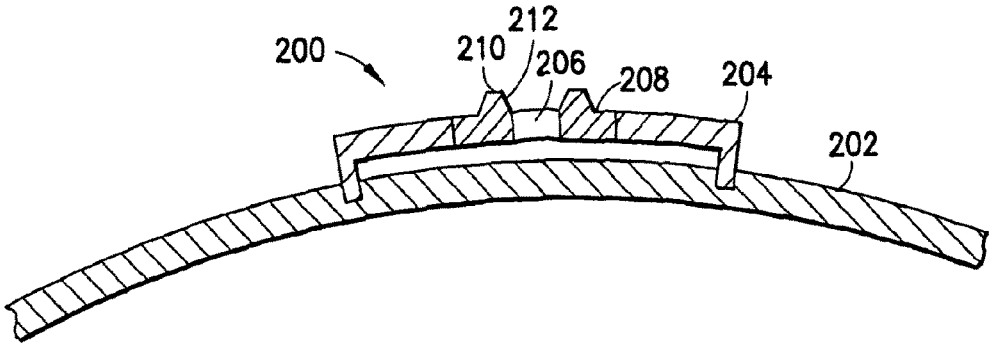
FIG. 4 is a cross-section of an embodiment of the invention in which the template is used in cranial surgery.

For example, the method can be used in stereotaxic surgery, e.g., intracranial surgery, as shown in FIG. 4. In this embodiment, a template, shown generally at 200 in FIG. 4, can be mounted to a patient's head 202 by a frame 204. Template 200 may include a guideway, 206 through a removable portion 208 in template 200, similar to the components of the embodiments illustrated above. Removable portion 208 may also include a stop 210, preferably having tapered shoulders 212 to countersink a drill bit used therein.

In a further embodiment, the method can be used to manufacture a surgical template with a method for the creation of a specific form of a radiographic stent that depends on the dual registration of the upper and lower tooth surfaces into an occlusal wafer that is a standard surgical type of splint. However, in this application a skirt is added to the buccal (lateral) aspects of the surgical splint. Six radiographic markers are placed on the radiographic splint for registration. The patient has the radiographic stent inserted into his teeth and his jaws are wired shut. The patient undergoes a CT scan and, after the scan, the radiographic occlusal splint is removed and scanned separately and then reinserted into the patient's jaws and the teeth are wired shut again into the radiographic splint. The two data sets are then merged by using the radiographic markers as the points of alignment. The result is that the plastic template has the memory of the negative impression of the teeth which is registered in the CT scan data and allows for a replication of the tooth form that would otherwise be unobtainable accurately for the reasons described above. The practitioner then decides on the appropriate trajectory of the surgical fixation screws which is registered and allows the manufacturing process to convert the data of the radiographic template into a surgical template with appropriate trajectories prepared in the correct sites where the surgical fixation screws will be placed via a drilling procedure through metal sleeves to be inserted in the surgical template. The virtual surgical template is sent for manufacturing to produce the surgical template that will be inserted in the patient's mouth for precise placement of surgical screws in the jaw bone via a drilling and insertion procedure that will then allow the placement of an external fixation device and the patient can have his jaws unwired.

Considerable time and cost savings are achieved because the original radiographic stent can be used for both the CT scan and the surgical procedure. The cost of the surgical template is significantly lowered because the time for rapid manufacturing is substantially decreased, allowing more modular templates to be fabricated with less material than would be necessary to create an entire replica of the radiographic splint with trajectories. Greater accuracy is also possible by using the original radiographic splint to fit into the patient's mouth or to remain bolted to the cranium.

This accuracy and cost savings can be applied to a method in which based on a CT scan, a treatment plan can be created whereby the dental implants will be placed and prosthesis inserted all within the same practitioner visit, which saves the patient and practitioner considerable savings in time and costs. In this method, the CT scan is obtained as described above and the surgical template created from the modular portion and the prosthesis which has been fabricated from dental models and based on the stereolithographic model merged with a dental cast to create a laboratory fabricated dental prosthesis. This can be extended to the creation of epthithesis for the replacement of other body parts, e.g., noses, eyes and ears.

The modular portion data can be used to create a temporary bridge or denture type of prosthesis with a modular component. A separate processing of the data creates a modular portion that, instead of having drill trajectories, includes a modular section that can become the attachment element of a dental implant prosthesis, disposed along the same trajectory paths which indicate the planned implant positions. Various means can be utilized to create the implant prosthesis interface of attachment. One method, described by Nobel Biocare, is to utilize a 2-part split shank abutment whereby when a screw is inserted through the dental prosthesis through this 2-part split shank abutment, compensation for the inaccuracy of the fit is achieved between the actual insertion of the implant in the bone and its position relative to the planned prefabricated temporary dental implant prosthesis.

Another method is described based on the slotted slot method of bone plate fixation in which the slot is an inclined curved plane and the screw is half a hemispheric head. In this embodiment, both the superior and inferior aspects of the manufactured modular section have slots. The inferior slot attaches to an adjustable implant abutment and the superior slot has a fixation screw driven through it that inserts into the threaded head of the implant abutment. This dual slotted system allows fixation of the implant prosthesis with compensation for any inaccuracies in the prefabrication of the implant prosthesis. The implant abutment is either a 2-part adjustable threaded member with locking screw adjusted up to the level of the inferior slot, or threads into a threaded interior of the inferior slot similar to a locking plate, with a slit shank or 3-part member inferior aspect of the implant abutment which acts as an intermediate washer.

Figure 5:
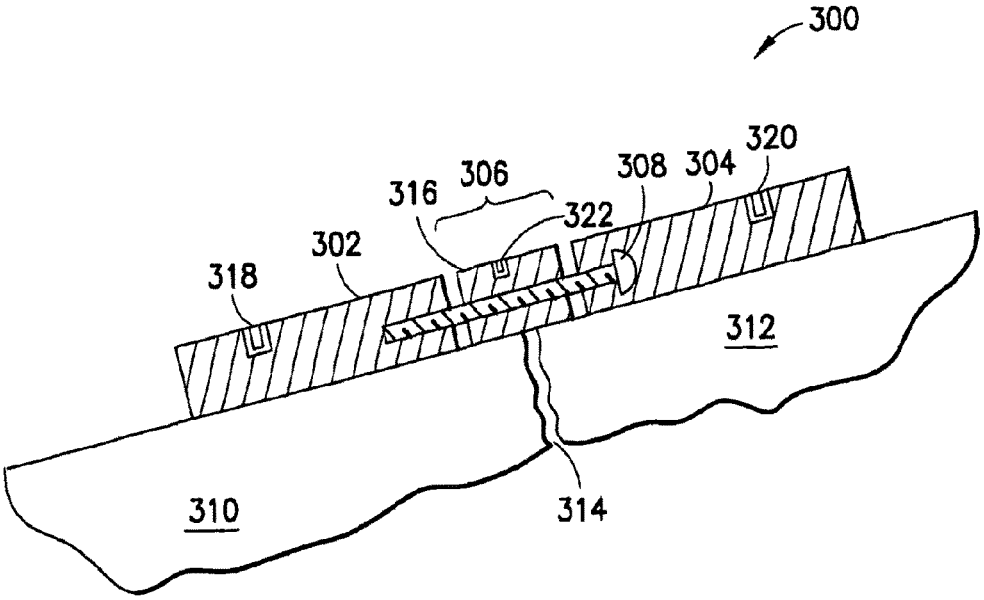
FIG. 5 is a partial cross-section of a further alternate embodiment of the invention useful in providing distraction osteogenesis.

A further application of the inventive template in distraction osteogenesis is shown in FIG. 5. In this type of application, it is desired to provide for gradual movement and lengthening of a base, through a series of breaks in the base, followed by a slight separation of the broken portions. The base then knits to fill in the small separation, lengthening the base. This process is repeated, as necessary, to lengthen the base to a desired degree.

A template for assisting in distraction osteogenesis is shown in FIG. 5, generally at 300. Template 300 includes two discontiguous sections 302, 304 separated by a variable gap 306, and connected by an adjustment device, such as an Archimedes screw 308. Applying rotation to Archimedes screw 308 imports linear motion to separate sections 302, 304 or bring them closer together, and thereby change the spacing of gap 306. Sections 302, 304 are mounted to respective body sections 310, 312 having a gap 314 therebetween. A modular section 316 may be inserted into gap 306, for example, to steady sections 302, 304 or for use in assisting in taking radiographs of the surrounding body 310,

312 to determine the progress of the procedure. If desired, radiographic makers 318, 320 and 322 may be positioned in sections 302, 304 and modular section 316, respectively, for this purpose.

It will be appreciated that various modifications of the method and apparatus described above can be made without departing from the scope and teachings contained herein. For example, it is possible for the dimensions of the guideway and/or any ferrules placed therein to be varied in diameter to accommodate instruments having different diameters.

It is also possible to utilize only a single sleeved element in lining the guideway so that, for example, in the embodiment of FIG. 3, inner piece [136] *138* would be optional. The provision of the metal sleeve would permit the use of a durable, for example, metal, outer piece 140 to prevent distortion of the interior of the guideway, and thereby maintain the integrity of the trajectory formed thereby.

Thus, while there have shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

What is claimed is:

1. A template for use with an instrument for penetrating an uncut irregular surface through a hole in said uncut irregular surface, said hole being located at a desired location on said uncut irregular surface, said template comprising:

a body including a custom surface shaped as a negative impression of the uncut irregular surface to conform to the uncut irregular surface, the body having a receiving section;

a removable portion configured to seat in the receiving section of the body;

said body further including a guideway that is detachably connected to the removable portion and having a first end positioned to open onto said desired location when said body is placed in conforming contact with said uncut irregular surface;

said guideway having a second end positioned on an exterior surface of said body, and connected to said first end by a passage;

a radiographic marker arranged in the removable portion;

means for securing said removable portion to said body;

a stop for limiting a depth of penetration of said instrument into said hole; and wherein the guideway comprises an inner piece including the stop, and an outer piece, and wherein the outer piece includes a threaded inner surface configured to engage threads on a threaded outer surface of the inner piece, and a threaded outer surface.

2. The template of claim 1, wherein said guideway is substantially linear.

3. The template of claim 1, wherein said stop is integrally formed with said inner piece.

4. The template of claim 1, wherein said template is intended for use in surgery.

5. The template of claim 4, wherein said uncut irregular surface is a surface of a bone.

6. The template of claim 5, wherein said bone is a jaw.

7. The template of claim 5, wherein said bone is a cranium.

8. A modular template for use with a drill bit for drilling a hole into an uncut irregular surface at a desired location on said uncut irregular surface, said template comprising:

a body including a custom surface shaped as a negative impression of the uncut irregular surface to conform to the uncut irregular surface and a removable portion;

said body further including a guideway that is detachably connected to the removable portion and having a first end positioned to open onto said desired location when said body is placed in conforming contact with said uncut irregular surface;

said guideway having a second end positioned on an exterior surface of said body, and connected to said first end by a passage;

said guideway being positioned in said removable portion; and means for attaching said removable portion to said body, wherein each of said body and said removable portion includes a radiographic marker such that said body comprises a radiographic template for subsequent removable portions, wherein the guideway comprises an inner piece and an outer piece, and wherein the outer piece includes a threaded inner surface configured to engage threads on a threaded outer surface of the inner piece, and a threaded outer surface.

9. The template of claim 8, wherein said means for attaching includes a clip.

10. The template of claim 8, further comprising:

a stop for limiting a depth of penetration of said drill bit into said hole, the stop attached to the inner piece.

*11. A template for use with an instrument for penetrating an uncut irregular surface through a hole in said uncut irregular surface, said hole being located at a desired location on said uncut irregular surface, said template comprising:*

*a body including a custom surface shaped as a negative impression of the uncut irregular surface to conform to the uncut irregular surface, the body having a receiving section;*

*a removable portion configured to be arranged in the receiving section;*

*a removable guideway arranged at the removable portion and having a first end positioned to open onto said desired location when said body is placed in conforming contact with said uncut irregular surface, wherein the removable guideway comprises an inner piece and an outer piece, and wherein the outer piece includes an outer surface configured to engage an inner surface of the removable portion;*

*means for securing said removable portion to said body; and*

*the inner piece configured as a stop for limiting a depth of penetration of said instrument into said hole.*

*12. The template of claim 11, wherein the inner piece comprises a ferrule.*

*13. The template of claim 12, wherein the stop is integrally formed with the ferrule.*

*14. The template of claim 12, wherein the guideway is substantially linear.*

*15. The template of claim 11, wherein the uncut irregular surface is a surface of a bone.*

*16. The template of claim 15, wherein the bone is a jaw.*

*17. The template of claim 11, further comprising: a modular portion configured as an attachment element of a dental implant prosthesis.*

*18. The template of claim 11, further comprising: a radiographic marker arranged in the removable portion.*

*19. A modular template for use with a drill bit for drilling a hole into an uncut irregular surface at a desired location on said uncut irregular surface, said template comprising:*

*a body including a custom surface shaped as a negative impression of the uncut irregular surface to conform to the uncut irregular surface;*

*a guideway that is detachably connected to the body and having a first end positioned to open onto said desired location when said body is placed in conforming contact with the uncut irregular surface, wherein the guideway comprises an inner piece, which is configured as a removable stop, and an outer piece, and wherein the outer piece includes an outer surface fastened to an inner surface of the guideway;*

*the guideway having a second end positioned on an exterior surface of the body, and connected to the first end by a passage; and*

*the removable stop for limiting a depth of penetration of said instrument into said hole.*

*20. The template of claim 19, wherein at least the body includes a radiographic marker such that the body comprises a radiographic template.*

*21. The template of claim 19, further comprising: a connector configured to attach the guideway to the body.*

*22. The template of claim 19, further comprising: a modular portion configured as an attachment element of a dental implant prosthesis.*

* * * * *